United States Patent [19]

Eckhouse et al.

[11] Patent Number: 5,849,029
[45] Date of Patent: Dec. 15, 1998

[54] METHOD FOR CONTROLLING THE THERMAL PROFILE OF THE SKIN

[75] Inventors: Shimon Eckhouse; Eli Talmor, both of Haifa, Israel

[73] Assignee: ESC Medical Systems, Ltd., Yokneam, Israel

[21] Appl. No.: 578,754

[22] Filed: Dec. 26, 1995

[51] Int. Cl.$^6$ .................................................. A61F 7/00
[52] U.S. Cl. .................................... 607/104; 607/114
[58] Field of Search ........................ 606/9, 10, 13–19; 128/898–899; 604/20, 22; 607/104, 114

[56] References Cited

U.S. PATENT DOCUMENTS

| | | |
|---|---|---|
| 5,057,104 | 10/1991 | Chess . |
| 5,282,797 | 2/1994 | Chess . |
| 5,330,519 | 7/1994 | Mason et al. ........................... 607/104 |
| 5,344,418 | 9/1994 | Ghaffari . |
| 5,405,368 | 4/1995 | Eckhouse . |
| 5,486,172 | 1/1996 | Chess . |

OTHER PUBLICATIONS

Selective Cooling Of Biological Tissues: Application For Thermally Mediated Therapeutic Procedures, B. Anvari, et al., Phys. Med. Biol. 40 (1995), pp. 241–252.

Cool Laser Optics Treatment Of Large Telangiectasia Of The Lower Extremities, J. Dermatol. Surg. Oncol. (1993), pp. 74–80.

Primary Examiner—Jeffrey R. Jastrzab
Assistant Examiner—Ryan Carter
Attorney, Agent, or Firm—Friedman Siegelbaum LLP

[57] ABSTRACT

A method is provided for cooling skin during irradiation treatment including thermally coupling a window to the skin and actively extracting heat from the window. The window may be transparent to therapeutic wavelengths transmitted to and through the window and to the skin below. An apparatus for therapeutic treatment of skin tissue is provided, including a source of electromagnetic radiation, a window transparent to the radiation coupled to the skin being treated to remove heat from the skin, coolant fluid coupled to the window to extract heat from the window, and a heat exchanger thermally coupled to the coolant to remove thermal energy from the coolant.

4 Claims, 2 Drawing Sheets

SECTION A-A

METHOD FOR CONTROLLING THE THERMAL PROFILE OF THE SKIN

This invention relates to a method and apparatus for controlling the thermal profile of skin. More particularly, it relates to a method of reducing the temperature of an outer layer of skin while the temperature of an inner layer of skin is elevated.

FIELD OF THE INVENTION

Electromagnetic radiation is used to treat a variety of skin disorders, such as vascular and pigmented lesions, hair removal, skin rejuvenation, psoriasis, among others. This radiation is typically applied to the surface of the skin from a variety of radiation sources, such as lasers that emit coherent light, flashlamps emitting incoherent light and microwave radiation sources, among others. Whatever the source of electromagnetic radiation, in order to provide treatment without damaging the epidermis and surrounding tissue, careful consideration must be given to the problem of maintaining the proper thermal profile in the skin.

For example, a method called selective photothermolysis uses selective absorption of pulses generated in the visible and near-visible ranges of electromagnetic spectrum to produce selective thermal injury to the skin. In this treatment, the skin is exposed to short pulses of electromagnetic radiation to heat tissue chromophores and blood vessels. Short pulses of intense radiation are necessary to transmit energy to the target tissue at a level that can damage the tissue before it can be cooled off. Since the cooling time for the epidermis is typically around 9 milliseconds, the pulses must provide extreme localized heating. Repeated pulses of a few milliseconds duration followed by delays of a few tens of milliseconds provide optimal deep skin heating while minimizing damage to outer skin layers. By controlling the pulse width, pulse delay, energy per pulse, and the frequency of radiation applied to the skin, the temperature distribution of the skin as a function of depth —the thermal profile of the skin —can be controlled to prevent damage to the skin, while providing enough thermal energy for treatment.

As the depth of the tissue to be treated increases, so does the need to cool the outer layers of skin to prevent injury. Therefore, when treating skin greater then one millimeter deep, positive cooling of the epidermis may be required. There are three basic methods employed to cool the epidermis: cooling using a layer of radiation transparent gel; cooling using "ice cubes"; and cryogen spurt cooling.

In the first of these methods, cooling with a gel, a pre-cooled transparent gel is applied to the surface of the skin to conduct heat away from the epidermis into the gel. This method is limited by its ability to reduce the epidermis temperature by no more than about 20° Celsius. This limited cooling may not be sufficient if the treatment includes intense heating. In addition, it is cumbersome to apply the gel during treatment while simultaneously irradiating the skin. A further drawback is the passive nature of the cooling: heat is extracted from the skin into a precooled material in contact with the skin that heats up as the skin cools down. As thermal energy is conducted into the gel from the skin, the gel heats up until it reaches a temperature near body temperature. No method is provided to actively extract heat from the gel itself thereby maintaining it at a low temperature.

The second of these methods, cooling using "ice cubes", involves placing thin transparent ice cubes, approximately 5–7 millimeters thick, in contact with the skin. Applying the ice cubes and maintaining the proper contact with the skin is also cumbersome and difficult. Timing the cooling relative to the radiation pulses is also difficult to control. This method, too, is passive, since the heat transfer is limited to the thermal capacity of the ice itself. No means for actively extracting heat from the ice in contact with the skin is provided.

The third method, cryogen spurt cooling, involves spraying the surface of the skin being treated with a refrigerant, such as R-12, that evaporates at room temperature and pressure. The refrigerant is sprayed on the epidermis in pulses that typically vary between 5 and 80 milliseconds in duration. These pulses cool a surface area of skin of about seven millimeters in width. Since this method involves spraying a pressurized liquid coolant on the skin, the timing of cooling with respect to treatment irradiation is more controllable than the foregoing methods. A further advantage is the amount of cooling possible using this method; commonly used refrigerants can cool the epidermis as much as 40° Celsius. Drawbacks to this method include difficulty in controlling the amount of cooling, the inability to cool more than a small area of skin, and the difficulty in properly aligning the cooling and heating mechanisms.

The foregoing illustrates the need for a new method of cooling the skin that is more convenient, provides better control of temperature and timing, and is capable of cooling a larger surface area of skin.

SUMMARY OF THE PRESENT INVENTION

The present invention is directed to a method of cooling skin as protection against thermal damage during radiation treatment, and includes the steps of thermally coupling a window to the skin, and actively extracting heat from the window. To extract heat, a coolant fluid can be thermally coupled to the window and its heat may be conducted into the coolant fluid. The fluid, in turn, may be conducted away from the window by a pump, for example, and its flow may be regulated by a valve. Thermal energy may be removed from the coolant fluid, such as by coupling the fluid to a heat exchanger, for example, a thermoelectric cooler. Skin temperature can be monitored, such as by transmitting infrared radiation from the skin through the window, then electronically sensing this radiation. A thermally conductive gel may be interposed between the skin and the window, the window pressed against the skin, and a portion of the gel extruded from between the window and the skin. This gel may be a water-based thermally conductive gel, and may contain antifreeze.

The present invention is also directed to a method for controlling the depth-wise temperature distribution of skin tissue by thermally coupling skin tissue to a window that is transparent to therapeutic wavelengths of electromagnetic radiation, applying therapeutic wavelengths of radiation to the window, transmitting the wavelengths through the window, and applying the wavelengths to the skin tissue. The method may also include extracting thermal energy from the skin tissue by cooling the window a predetermined period before the radiation is applied to and transmitted through the window and applied to the skin.

In addition, the present invention is directed to an apparatus for therapeutic treatment of skin tissue including a source of therapeutic radiation, a window transparent to the radiation, coolant fluid thermally coupled to the window and adapted to remove thermal energy from the window, and a heat exchanger thermally coupled to the coolant to remove thermal energy from the coolant. The window may have a crystalline structure, such as sapphire or quartz. It may be a synthetic sapphire. It preferably transmits radiation in the 0.3 to 4.5 micron band of radiation. The window's thermal conductivity is preferably at least 10 W/m*° C. More preferably it is at least 25 W/m*° C. Nost preferably it is at least 40 W/m*° C. A conduit may be thermally coupled to the window and adapted to convey the coolant into thermal contact with the window. The coolant flow may be regulated, such as by a valve. A coolant moving element may be provided to propel the coolant through the conduit, such as a pump. The radiation source may emit incoherent electromagnetic radiation, such as a flashlamp, or may emit coherent radiation, such as a laser. The coolant may be thermally coupled along a lateral edge of the window. The window itself may transmit the coolant fluid, and may transmit fluid through the radiation path. The present invention may incldue a heat exchanger thermally coupled to the window to remove thermal energy from the window, and cooling fluid coupled to the heat exchanger to remove heat from the heat exchanger. The heat exchanger may be a thermoelectric cooler, and the coolant fluid may be air or a liquid. If the coolant fluid is a liquid, it is preferably maintained in thermal contact with the heat exchanger by a liquid conduit.

Other principal features and advantages of the invention will become apparent to those skilled in the art upon review of the following drawings, the detailed description and the appended claims.

Figure 1:
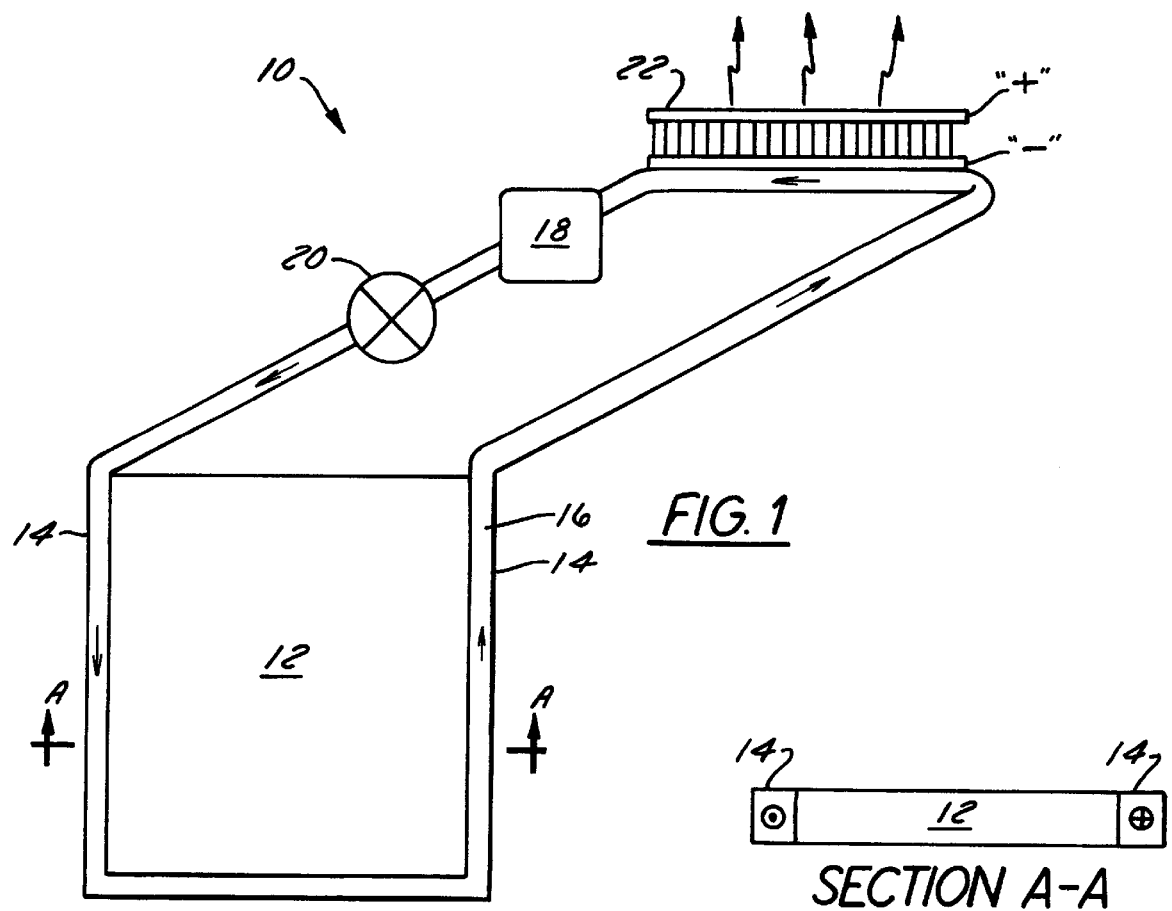
FIG. 1 is an illustration of an apparatus for cooling epidermis.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

The present invention is directed to a method and apparatus for cooling skin during electromagnetic irradiation treatments. Regarding FIG. 1, a cooling system 10 includes a transparent window 12 thermally coupled to a cooling channel 14. Cooling channel 14 contains a coolant 16, which is propelled through channel 14 by coolant pump 18, and is also regulated in its flow by coolant valve 20. A heat exchanger 22 is provided to regulate the temperature of coolant 16.

The transparent window serves two primary purposes in the present invention: conducting heat away from the skin, and transmitting electromagnetic radiation from a radiation source (not shown) to the skin for treatment. It is "transparent" in the sense that it allows desired therapeutic wavelengths of electromagnetic radiation to substantially pass from the radiation source to the area of skin being treated. To provide superior heat conduction and high radiation transmissivity, window 12 has a thermal conductivity of at least 10 W/m*° C. is preferred to provide the necessary cooling capacity for typical applications. A material having a thermal conductivity of at least 25 W/m*° C. (such as synthetic sapphire) is more preferred. Several commonly available crystalline materials such as quartz or sapphire provide even better cooling, and have thermal conductivities of around 40–45 W/m*° C. From a technical perspective, the best window material currently known is diamond, which has a thermal conductivity of around 900 W/m*° C. Diamond windows are currently impractical due to cost, however.

Sapphire's applicability is enhanced by its relative transparence to radiation in a band extending from 0.3 to 4.5 $\mu$m, enabling its use with a variety of coherent and incoherent radiation sources. The operation of a sapphire window is highly efficient. For example, a sapphire window measuring 35 mm by 8 mm and having a 5 mm thickness can be cooled to 0° Celsius from room temperature in less than 20 seconds, so that its temperature distribution will be highly uniform.

Cooling channel 14 is designed to contain coolant 16 and to thermally couple it to window 12, thus allowing heat transmitted from the skin to the window to be transferred into the coolant for removal from the treatment site. In the preferred embodiment, and as shown in FIG. 1, cooling channel 14 is formed along a lateral edge of window 12. Alternatively, cooling channel 14 may be integrally formed within window 12 itself. If a portion of cooling channel 14 passes through window 12 and coolant 16 is transparent to the therapeutic radiation, therapeutic radiation can be directed through both window 12 and coolant 16 to irradiate the treatment site.

Coolant 16 typically includes a high heat capacity fluid such as water. In this embodiment, it removes heat from the skin by conduction from the window. To transfer thermal energy from the treatment site to the window, the window must be maintained at a temperature below that of the treatment site. To transfer thermal energy from the window to the coolant, the coolant must be maintained at a temperature below that of the window. To significantly limit damage to the skin during treatment, the treated skin should preferably be cooled to a temperature at or near the freezing point of water. To provide a temperature this low, the coolant must remain fluid at a temperature of 0° Celsius or below. Thus the coolant preferably includes an antifreeze. If the coolant is conducted through channels in the window itself, rather than along the lateral edges of the window, it should preferably be transparent to radiation in the band of therapeutic wavelengths.

Coolant pump 18 is provided to pump coolant 16 through cooling channel 14 in the direction of the arrows shown in FIG. 1, and valve 20 regulates the flow of coolant through the cooling channel. Cooling can be controlled by regulating the output of the pump, typically by regulating pump speed or capacity, regulating the amount of flow restriction provided by the cooling valve or regulating both the pump and the cooling valve simultaneously. Preferred pumps include reciprocating, centrifugal and peristaltic pumps.

In the preferred embodiment, heat exchanger 22 is provided to transfer heat energy to a secondary cooling fluid such as air or water. The heat exchanger illustrated here is a thermoelectric cooler which, due to its relatively small size and low power consumption, is particularly suited to removing heat energy from the coolant. In this embodiment, the coolant is in a closed loop, picking up heat at the window and releasing heat in the heat exchanger. By regulating the current flowing through the thermoelectric cooler (which is produced in the embodied heat exchanger by application of a voltage to its terminals labeled "+" and "−") the amount of heat extracted from the coolant can be varied. In an alternative embodiment, rather than providing a closed loop for the primary coolant, an large reservoir of chilled coolant can be provided to cool the skin. In this alternative embodiment, the heat exchanger would be replaced with a large precooled reservoir or tank of coolant. Fluid would be pumped out of this reservoir and through the window.

Figure 2:
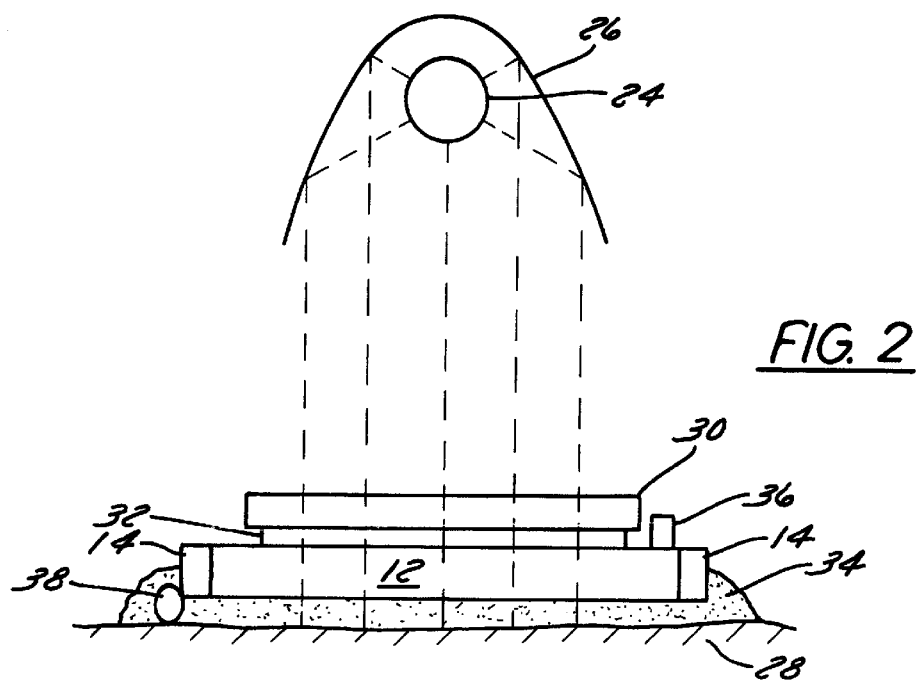
FIG. 2 is a cross-sectional view of a device for the treatment of lesions including the apparatus of FIG. 1 thermally coupled to the skin at a treatment site.

FIG. 2 discloses another embodiment of the invention including a radiation source 24 for emitting electromagnetic radiation, a reflector 26 for reflecting the radiation toward a treatment site 28, a light guide 30 for directing and transmitting the radiation toward treatment site 28, a radiation filter 32 for restricting the radiation transmitted to therapeutic bands of frequencies, window 12 for transmitting the therapeutic wavelengths toward treatment site 28 while simultaneously conducting thermal energy from the skin, a gel 34 for transmitting the therapeutic radiation wavelengths while simultaneously conducting thermal energy from the skin to window 12, a radiation sensor 36 for sensing the temperature of treatment site 28, cooling channels 14 and pressure sensor 38. The path of therapeutic radiation emitted from radiation source 24 to the treatment site is shown schematically as dashed lines. Coolant passing through the cooling channels can be conveyed, controlled and cooled in a manner similar to that disclosed in FIG. 1 and the accompanying text.

Radiation source 24 provides pulsed electromagnetic radiation including therapeutic wavelengths of radiation. In this embodiment, radiation source 24 is a flash lamp that emits incoherent radiation in a broad spectrum. Alternatively, a radiation source capable of providing coherent radiation, such as a laser radiation source, may also be effectively employed.

Reflector 26 is preferably polished metal, for example polished aluminum, to reflect at least the radiation in therapeutic wavelengths.

Light guide 32 is employed to gather and direct radiation from the radiation source to treatment site 28. Typically an optical fiber is employed for radiating relatively small treatment sites, and a quartz light guide is employed for radiating larger treatment sites.

Radiation filter 32 is employed to filter out unwanted wavelengths of radiation, typically wavelengths that are harmful to the skin, such as radiation in the ultraviolet spectrum. One or more filters may be employed to transmit a band of wavelengths that are tailored to penetrate the skin to a predetermined depth.

A gel 34 may be disposed between the surface of the skin and the window, thermally coupled to both, to provide better transmission of therapeutic wavelengths by reducing backscatter off the surface of the window in proximity to the skin and to provide more effective conduction of thermal energy from the skin to the window by eliminating pockets of air that may remain between skin at the treatment site and window 12. Skin at the treatment site is often rough and uneven. Consequently, pockets of air (not shown) may remain between window 12 and skin at the treatment site preventing good thermal contact when window 12 is pressed against the skin. Heating and cooling may be uneven and unpredictable. A wetting agent, such as gel 34, when applied between window 12 and skin at the treatment site, fills surface imperfections on the skin, and allows air to be expelled when window 12 is pressed against the skin. Water-containing gels are particularly effective due to their relatively high thermal conductivity, their ability to wet both the treatment site and the window, and their ability to transmit a wide range of therapeutic radiation wavelengths. In use, a gel is applied to the window or the skin in quantities greater than that needed to fill the surface imperfections, then the window is brought into contact with the skin. As pressure is applied to the window, excess gel (along with entrained air) is squeezed out along the sides of the window, providing a thin, thermally conductive layer of gel between the window and the treatment site.

Radiation sensor 36 may be employed to produce a signal indicative of the degree of skin heating or cooling. A sensor responsive to infrared wavelengths of light emitted by skin at the treatment site is particularly well suited to this application. The window is preferably oriented between the sensor and the treatment area to pass thermal radiation emitted from the skin to the sensor. Radiation sensors that are responsive to radiation in the 2 to 5 micron band are particularly suitable for measuring radiation emitted from the skin.

Cooling channels 14 may be employed as described above in accordance with the description in accompanying FIG. 1.

In order to achieve good thermal contact with the skin surface, it is preferable to apply and maintain pressure on the window against the treatment site. Pressure sensor 38 is disposed to sense this pressure. In this embodiment, it is fixed with respect to the window. Since the pressure sensor indicates contact between the window and the treatment site, it can be monitored to indicate the onset of skin cooling and thus to control a delay (if desired) between cooling and generation of the therapeutic radiation. For example, epidermis at a 50 micron depth can be cooled from 32° Celsius to 6° Celsius in 1 second. By delaying the light pulse for 1 second after cooling initiation, significant damage to the epidermis layer can be avoided. Window temperature is also a factor in determining the light pulse delay. For example, if the window is cooled to −15° Celsius before it is applied to the skin, the time to cool the epidermis at a depth of 100 microns is reduced to 0.1 seconds. By monitoring the pressure sensor, and controlling the temperature of the window, optimal cooling can be provided.

Figure 3:
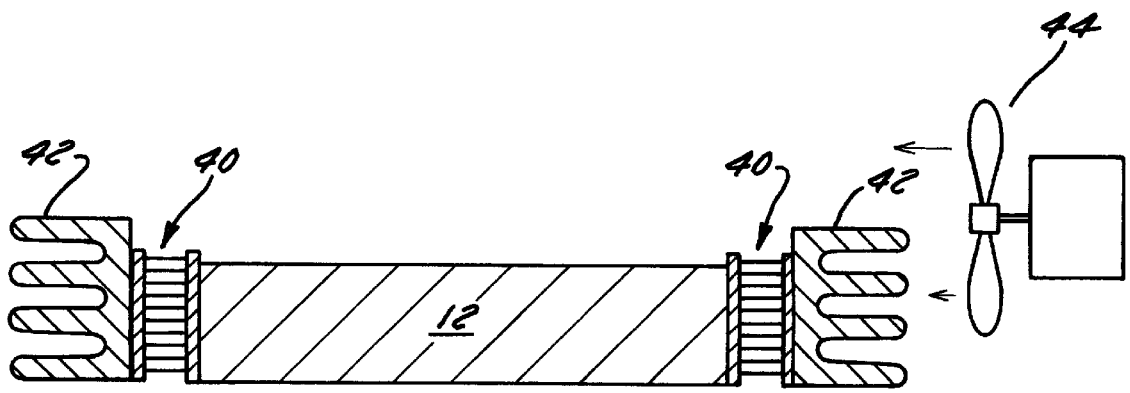
FIG. 3 is a cross-sectional view of a window with a thermally coupled heat exchanger and heat sink.

FIG. 3 discloses a cross-sectional view of window 12, thermally coupled to heat exchanger 40, with attached heat sink 42. A fan 44 is provided to blow air across heat sink 42. In this embodiment, unlike the embodiment show in FIGS. 1 and 2, heat exchanger 40 (here shown as a thermoelectric cooler) is thermally coupled to window 12 directly, eliminating the intermediate coolant shown in FIG. 1 and indicated in FIG. 2. This apparatus is preferred when a quick response is required and it is possible to apply a large window to the treatment site. By thermally coupling heat exchanger 40 directly to window 12, it can cool the window directly. In comparison, the apparatus disclosed in FIG. 1 allows heat exchanger 22 to cool the window by first chilling coolant 16, which in turn cools window 12. In such an embodiment, both the mass of coolant 16 and the mass of window 12 must be chilled to a temperature below the desired skin temperature to effect cooling to that temperature. By placing heat exchanger 40 in direct thermal contact with the window 12, only the mass of the window need be cooled to a temperature below the desired skin temperature to effect cooling to that temperature. This direct coupling allows more rapid window cooling and more precise control of skin temperature. This improved cooling and control, in turn, provides for more rapid cycling of the radiation source (shown in FIG. 2) and shorter treatments. Heat exchanger 40 is preferably controlled similarly to the heat exchanger of FIG. 1.

To provide more rapid cooling and to increase the efficiency of heat exchanger 40, it may be thermally coupled to heat sink 42. A preferred material for the heat sink is aluminum or another high conductivity metal. Fins may be provided on heat sink 42 to enhance cooling.

Fan 44 may also be employed to increase the air flow about heat exchanger 40 to transfer heat away from the hot side of heat exchanger 40 or the fins of heat sink 42.

Since typical heat exchangers are not transparent to the common wavelengths of therapeutic radiation used for treatment, the heat exchanger or exchangers are preferably thermally coupled to the window along its lateral edges, thereby providing a path for the therapeutic radiation to reach the treatment site. Alternatively, a window larger than the treatment site can be provided, and the heat exchanger or exchangers can be coupled to an upper surface of the window adjacent to, but not obstructing, the path of the therapeutic radiation that passes through the window and impinges upon the skin.

Figure 4:
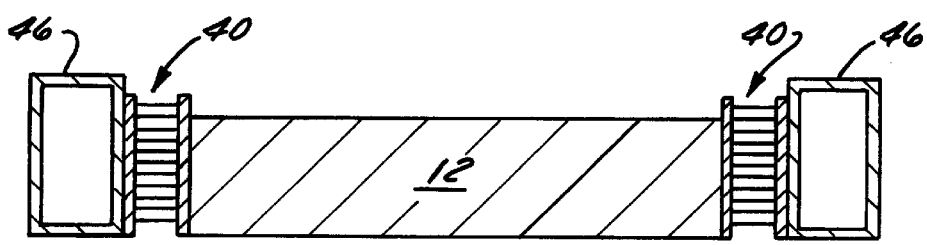
FIG. 4 is a cross-sectional view of a window with a thermally coupled heat exchanger and liquid conduit.

FIG. 4 discloses an alternative embodiment of window 12 and thermally coupled heat exchanger 40 similar to that of FIG. 3. In the FIG. 4 embodiment, fluid coolant flow (such as coolant 16, above) through cooling channel 46 removes heat from heat exchanger 40. Cooling channel 46 is thermally coupled to heat exchanger 40 to remove thermal energy from heat exchanger 40. The coolant may be drawn from an external reservoir of fluid. Heat exchanger 40 in this embodiment is a thermoelectric cooler capable of pumping heat from a cool side to a hot side of the device. Since heat is pumped from window 12 to cooling channel 46, the coolant in cooling channel 46 need not be maintained at a temperature below the target temperature of the skin, as is the case in the FIG. 1 embodiment. Thus, sources of coolant fluid warmer than that used in the FIG. 1 embodiment, such as a cold water tap, may be sufficient for many applications.

In an alternative embodiment, the window 12, heat exchanger 40 and cooling channel 46 of the FIG. 4 device can replace the window 12 and cooling channel 14 of the FIG. 1 device, thereby providing a system with two heat exchangers and an intermediate coolant. This will provide superior temperature control and a faster cooling response time than that provided by the FIG. 1 or FIG. 4 embodiments alone.

Thus, it should be apparent that there has been provided in accordance with the present invention a method and apparatus for cooling skin and the selective heating of lesions that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

We claim:

1. A method of cooling skin to protect the skin from thermal damage during irradiation treatment using therapeutic electromagnetic radiation including the steps of:

thermally coupling a window to the skin; and extracting heat from said window, including the steps of thermally coupling a cooling fluid to said window in a first, second and third path defined along and thermally coupled to a first lateral edge, a second lateral edge and a third lateral edge, respectively, of said window to thereby couple coolant for at least three quarters of a periphery of said window; conducting heat from said first, second and third lateral edges of said window to said coolant fluid; and conducting said coolant fluid away from said window after said step of conducting heat from said window to said coolant fluid.

2. The method of claim 1 wherein the first, second and third paths define a central window portion having a solid radiation conducting path between an upper and lower portion thereof.

3. The method of claim 1, wherein the first, second and third paths are defined by hollow elongate cooling channels coupled at their ends to provide a continuous flow path along said three lateral edges.

4. A method of cooling skin to protect the skin from thermal damage during irradiation treatment using therapeutic electromagnetic radiation including the steps of:

thermally coupling a window to the skin: and extracting heat from said window, including the steps of thermally coupling a cooling fluid to said window in a first, second and third path defined along and thermally coupled to a first lateral edge, a second lateral edge and a third lateral edge, respectively, of said window to thereby couple coolant for at least three quarters of a periphery of said window wherein the first and second paths are defined by hollow elongate coolant channels coupled at their ends to provide a continuous flow path along each of said lateral edge; conducting heat from said first, second and third lateral edges of said window to said coolant fluid; and conducting said coolant fluid away from said window after said step of conducting heat from said window to said coolant fluid.

* * * * *